United States Patent
Wang et al.

(10) Patent No.: US 7,519,146 B2
(45) Date of Patent: Apr. 14, 2009

(54) METHOD OF OBTAINING RADIOACTIVE ENERGY CURVE FOR REINFORCED CONCRETE AND APPARATUS THEREFOR

(75) Inventors: Chung-Yue Wang, Jhongli (TW); Peng-Ching Peng, Jhongli (TW)

(73) Assignee: National Central University, Jhongli (TW)

( * ) Notice: Subject to any disclaimer, the term of this patent is extended or adjusted under 35 U.S.C. 154(b) by 394 days.

(21) Appl. No.: 11/583,127

(22) Filed: Oct. 19, 2006

(65) Prior Publication Data

US 2008/0089475 A1    Apr. 17, 2008

(30) Foreign Application Priority Data

Oct. 14, 2006    (TW) ............... 95137838 A

(51) Int. Cl.
*G01J 1/00*    (2006.01)

(52) U.S. Cl. ............... 378/55; 250/359.1; 250/358.1; 250/360.1; 378/56; 378/62; 378/162; 378/163; 378/901; 378/207

(58) Field of Classification Search ............... 250/503.1, 250/359.1, 506.1, 515.1, 252.1, 358.1, 360.1, 250/306; 378/54–58, 62, 162, 163, 901, 378/207, 4–27, 1; 588/4, 15, 16; 252/478
See application file for complete search history.

(56) References Cited

U.S. PATENT DOCUMENTS

| 7,430,275 B2 * | 9/2008 | Wang ............... 378/56 |
| 2008/0197278 A1 * | 8/2008 | Wang et al. ............... 250/306 |
| 2008/0198962 A1 * | 8/2008 | Wang et al. ............... 378/1 |

* cited by examiner

*Primary Examiner*—Jack I Berman
*Assistant Examiner*—Meenakshi S Sahu
(74) *Attorney, Agent, or Firm*—Troxell Law Office, PLLC

(57) ABSTRACT

The present invention uses a penetrative radiation to form images of a reinforced concrete which has a steel bar. By recording a relationship between radioactive energies and thicknesses of the reinforced concrete, a radioactive energy curve for the reinforced concrete is built. The present invention can be used for an on-site detecting of a reinforced concrete.

10 Claims, 4 Drawing Sheets

| Thickness (cm) | Preferred Duration (sec) | Intensity ×Preferred duration (Ci*sec) |
|---|---|---|
| 10 | 6 | 450 |
| 15 | 12 | 900 |
| 20 | 21 | 1575 |
| 25 | 32 | 2400 |
| 30 | 46 | 3450 |
| 35 | 63 | 4720 |
| 40 | 82 | 6150 |

FIG.3

METHOD OF OBTAINING RADIOACTIVE ENERGY CURVE FOR REINFORCED CONCRETE AND APPARATUS THEREFOR

FIELD OF THE INVENTION

The present invention relates to detecting a steel bar; more particularly, relates to using a penetrative radiation for obtaining a relationship among radiation intensity, radiation duration and thickness of reinforced concrete and for further building a radioactive energy curve for the reinforced concrete.

DESCRIPTION OF THE RELATED ART(S)

Prior arts to the present invention include detections using ultrasonic wave, penetrating radar, transient elastic wave, and X-ray. But, the detection using ultrasonic wave may require big energy; and, on detecting an object having a thickness more than 40, signals may be too weak to be received. The penetrating radar is used in basic detection or in pavement detection. And, if the concrete is not homogeneous, noises will increase owing to diffractions. The transient elastic wave is hard to be used in detecting a concrete for it is highly non-homogeneous; so, diffractions and refractions are produced to rapidly weaken energy.

X-ray has a high energy and a strong penetrating ability; and its energy is adjustable for various size of object to obtain an accurate image. Yet, an X-ray machine is expansive and heavy and requires an energy source. Because its energy is high, it is not easy to apply for an on-site use. Hence, the prior arts do not fulfill users' requests on actual use.

SUMMARY OF THE INVENTION

The main purpose of the present invention is to use a penetrative radiation for obtaining a relationship among radiation intensity, radiation duration and thickness of a reinforced concrete and for further building a radioactive energy curve for the reinforced concrete.

To achieve the above purpose, the present invention is a method of obtaining radioactive energy curve for a reinforced concrete and an apparatus therefor. The method comprises steps of: (a) obtaining various thicknesses of a reinforced concrete having a steel bar and selecting a reinforced concrete having a thickness; (b) obtaining a radioactive detecting device of Ir-192, Co-60 or Cd-137; (c) radiating a penetrative ray having a radiation intensity of 75 Ci for durations of time to obtain images of the reinforced concrete; (d) examining the images for clearness of the steel bar; (e) obtaining a preferred duration from the various durations; (f) processing the other reinforced concretes through step (c) to step (e) separately; (g) obtaining records of radioactive energies (radiation intensities multiplied with preferred radiation durations) and thicknesses of the reinforced concrete; and (h) obtaining a radioactive energy curve for the steel bar from the records.

And, the apparatus for the method comprises a reinforced concrete with a steel bar; a radioactive detecting device comprising a radiation source having a radiation intensity to penetrate through the reinforced concrete; an imaging device to obtain an image of the reinforced concrete; and a data analyzer, where records showing a relationship between the preferred durations and radioactive energies are obtained and a radioactive energy curve is further built. Thus, a novel method of obtaining radioactive energy curve for a reinforced concrete and an apparatus therefor are obtained

BRIEF DESCRIPTIONS OF THE DRAWINGS

The present invention will be better understood from the following detailed description of the preferred embodiment according to the present invention, taken in conjunction with the accompanying drawings, in which FIG. 1 is the view showing the apparatus of the preferred embodiment according to the present invention;

FIG. 3 is the view showing the relationship among radiation intensities, radiation durations and thicknesses of the reinforced concrete.

DESCRIPTION OF THE PREFERRED EMBODIMENT

The following description of the preferred embodiment is provided to understand the features and the structures of the present invention.

Figure 1:
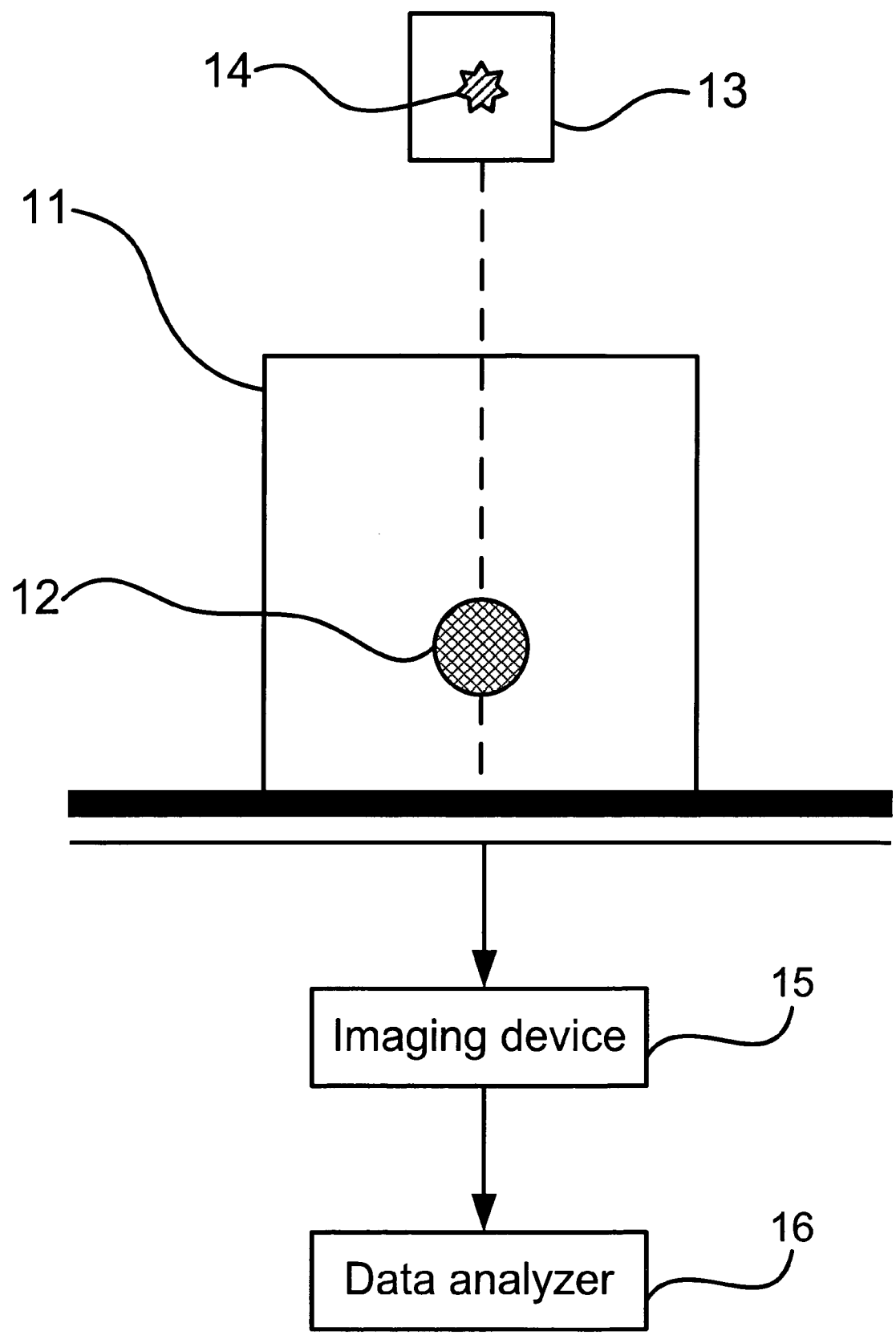

Please refer to FIG. 1, which is a view showing an apparatus of a preferred embodiment according to the present invention. As shown in the figure, the present invention is a method of obtaining radioactive energy curve for a reinforced concrete and an apparatus therefor. The apparatus comprises a reinforced concrete 11 having a steel bar 12; a radioactive detecting device 13 having a radiation source 14 with a radiation intensity penetrating the reinforced concrete 11; an imaging device 15 obtaining images after radiating the reinforced concrete 11 by the radiation source 14 for durations of time; and a data analyzer 16 examining the images to find a preferred duration, where a relationship between the preferred durations for various thicknesses of the reinforced concrete, and radioactive energies (i.e. the radiation intensity multiplied with the preferred durations) is recorded and a radioactive energy curve is further built.

Figure 2:
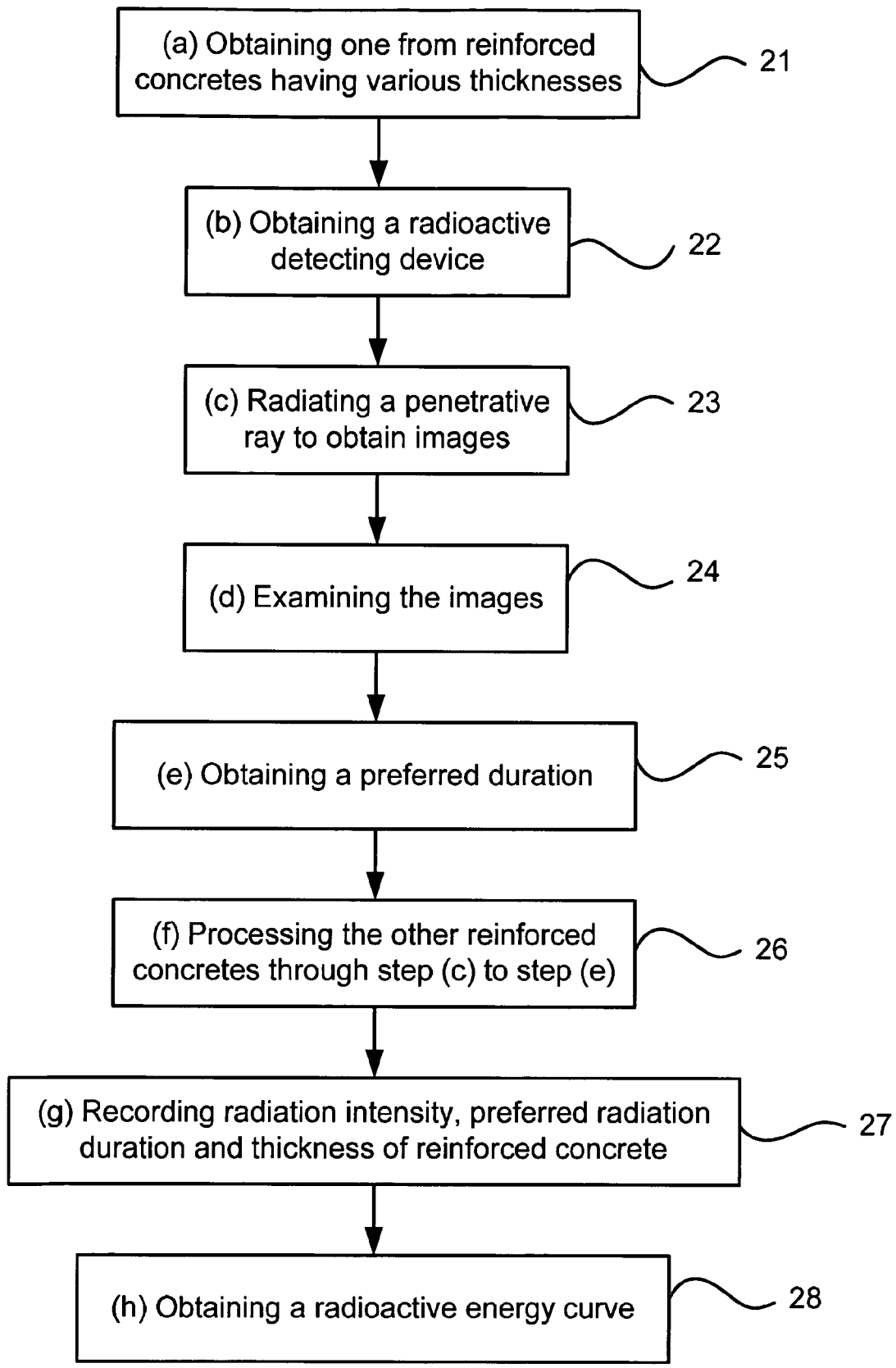
FIG. 2 is the flow view showing the method of the preferred embodiment.

Please refer to FIG. 2, which is a flow view showing a method of the preferred embodiment. As shown in the figure, a method of the preferred embodiment comprises the following steps:

(a) Obtaining a reinforced concrete from reinforced concretes having various thicknesses 21: Three reinforced concretes are made. They have sizes of 10 cm (centimeter)×10 cm×10 cm, 20 cm×10 cm×5 cm and 15 cm×10 cm×5 cm separately; a design strength of 280 kgf/cm$^2$; and a compressive strength of 310 kgf/cm$^2$. A steel bar is put in the reinforced concrete having the size of 10 cm×10 cm×10 cm, which has a length of 15 cm, a diameter of 1.2 cm and a thickness of a protecting layer of 5 cm. The three reinforced concretes are constituted to obtain various thicknesses of reinforced concrete containing the reinforced concrete of 10 cm×10 cm×10 cm. Therein, the reinforced concrete having the steel bar can be a reinforced concrete having a hole or a reinforced concrete having an artificial aperture; the various thicknesses are 10 cm, 15 cm, 20 cm, 25 cm, 30 cm, 35 cm and 40 cm. At first, a reinforced concrete of 10 cm is obtained to be processed with the following steps.

(b) Obtaining a radioactive detecting device 22: The radioactive detecting device obtained has a penetrative radiation source which is Ir-192, Co-60 or Cs-137 and has a radiation intensity of 75 Ci.

(c) Radiating a penetrative ray to obtain images 23: A penetrative ray having a radiation intensity is radiated for various durations of time to obtain images of the steel bar.

(d) Examining the images 24: The images are examined for clearness of the steel bar to find a qualified image.

(e) Obtaining a preferred duration 25: The duration for the qualified image is set as a preferred duration.

(f) Processing the other reinforced concretes through step (c) to step (e) 26: The other reinforced concretes having thicknesses of 15 cm, 20 cm, 25 cm, 30 cm 35 cm and 40 cm are processed through step (c) to step (e) separately.

(g) Recording radiation intensity, preferred radiation duration and thickness of reinforced concrete 27: Please refer to FIG. 3, which is a view showing a relationship among radiation intensity, radiation duration and thickness of reinforced concrete. As shown in the figure, a radiation intensity is multiplied with a radiation duration, which is a preferred duration for a reinforced concrete having a thickness, to obtain a radioactive energy. Thus, records showing relationships between preferred durations and radioactive energies for the reinforced concrete under various thickness are shown.

Figure 4:
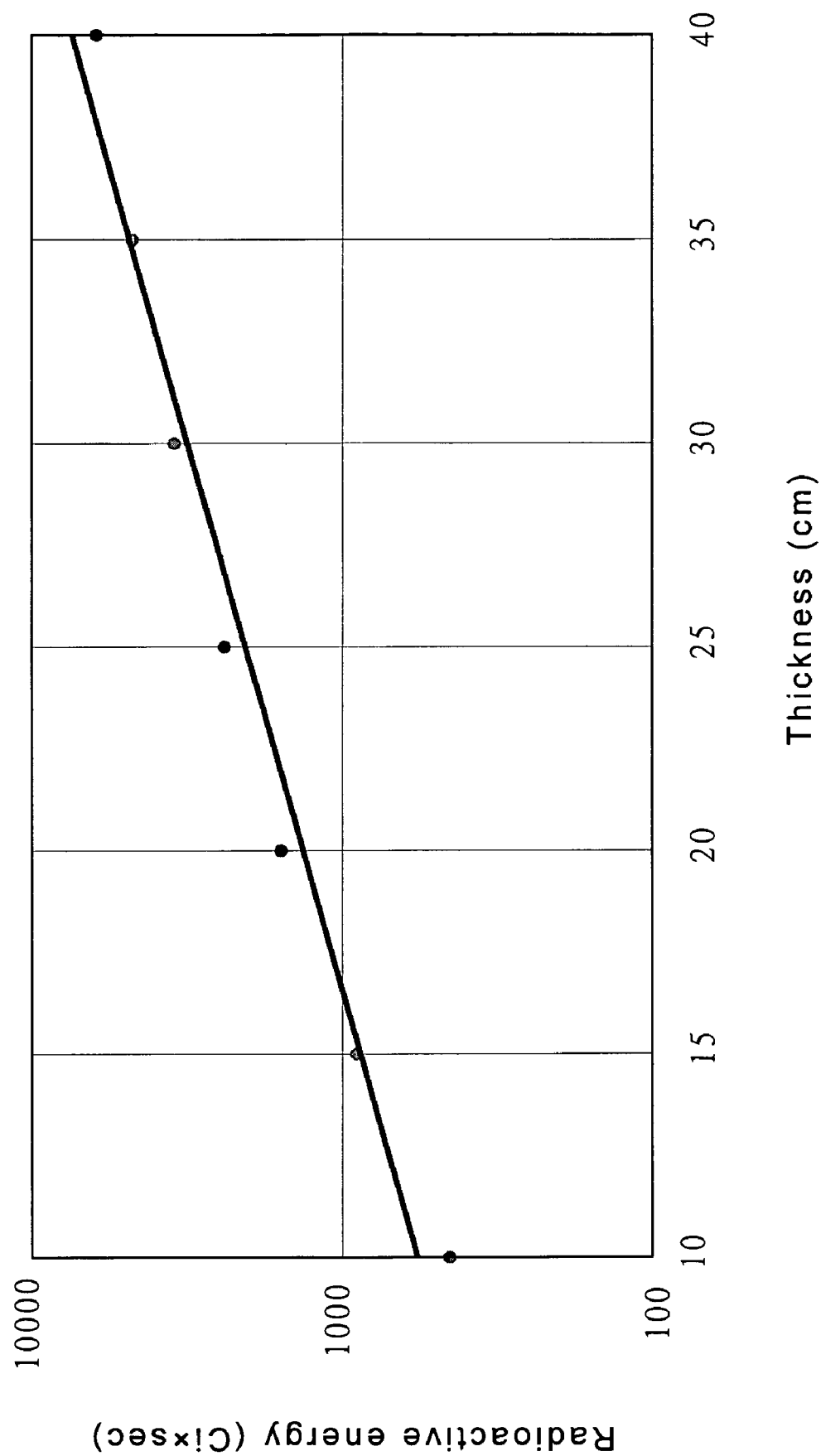
FIG. 4 is the flow view showing the radioactive energy curve for the reinforced concrete.

(h) Obtaining a radio active energy curve 28: Please refer to FIG. 4, which is a flow view showing a radioactive energy curve for the reinforced concrete. As shown in the figure, by using the records showing a relationship between preferred duration and radioactive energy for the reinforced concrete under various thickness, a radioactive energy curve is built and an experience formula is obtained as followed:

$$E=243.21e^{0.0853T}$$

where E is the radioactive energy and T is the thickness of reinforced concrete.

Thus, a novel method of obtaining radioactive energy curve for a reinforced concrete and an apparatus therefor are obtained. Hence, the present invention has the following characteristics:

(1) Reinforced concretes having various thickness are radiated with various radioactive energy to obtain reinforced concrete images.

(2) A penetrating radiation is used with low cost, high energy and uniform intensity; and requires no energy. The source of the radiation can be easily located in a complex structure to penetrate and detect a steel, an aperture, a hole, etc.

(3) Critical keys in the present invention are radiation intensity (M), preferred duration (T) and distance between radiation source and imaging device (t). A formula is obtained for figuring out changes in each element, as follows:

$$M_1 \times T_1 = M_2 \times T_2 = C (\text{constant } t)$$

where C is a radioactivity energy. Therefore, both of the radiation intensity and the preferred duration have a direct ratio to a square of a distance between the radiation source and the imaging device. And the radiation intensity has an inverse ratio to the preferred duration; that is, the higher the radiation intensity is, the shorter the preferred duration is.

To sum up, the present invention is a method of obtaining radioactive energy curve for a reinforced concrete and an apparatus therefor, where a penetrative radiation is used to obtain a relationship between a preferred duration of a radiation and a thickness of a reinforced concrete; and a radioactive energy curve is thus obtained to operate the present invention in a complex structure.

The preferred embodiment herein disclosed is not intended to unnecessarily limit the scope of the invention. Therefore, simple modifications or variations belonging to the equivalent of the scope of the claims and the instructions disclosed here in for a patent are all within the scope of the present invention.

What is claimed is:

1. A method of obtaining radioactive energy curve for a reinforced concrete, comprising steps of:
   (a) obtaining reinforced concretes having various thicknesses then selecting one from said reinforced concretes, said reinforced concrete having a steel bar;
   (b) obtaining a radioactive detecting device having a penetrative radiation source;
   (c) radiating a penetrative ray having a radiation intensity from said penetrative source on said reinforced concrete for various durations of time to obtain images of said reinforced concrete;
   (d) examining said images for clearness of said steel bar in said reinforced concrete to obtain a qualified image;
   (e) obtaining a preferred duration for said qualified image;
   (f) processing the other reinforced concretes through step (c) to step (e) separately;
   (g) obtaining records for said reinforced concretes separately, said record comprising a radiation intensity, a preferred duration and a thickness of reinforced concrete; and
   (h) obtaining a radioactive energy curve for said steel bar in said reinforced concrete.

2. The method according to claim 1,
wherein said reinforced concrete is further selected from a group consisting of a reinforced concrete having a hole and a reinforced concrete having an artificial aperture.

3. The method according to claim 1,
wherein said steel bar has a length between 12 centimeters (cm) and 18 cm, a diameter between 1 cm and 1.5 cm and a thickness of a protecting layer between 3 cm and 8 cm.

4. The method according to claim 1,
wherein said radiation source radiates a ray selected from a group consisting of Ir(Iridium)-192, Co(Cobalt)-60 and Cs(Cesium)-137; and
wherein said ray has a radiation intensity between 68 Ci(Curie) and 82 Ci.

5. The method according to claim 1,
wherein said preferred duration is a duration for a radiation to obtain an image among said images showing said steel bar the most clearly.

6. The method according to claim 1,
wherein radioactive energies are obtained by multiplying said radiation intensities with said preferred durations for said reinforced concretes having various thicknesses; and
wherein said radioactive energy curve is obtained from said radioactive energies.

7. The method according to claim 1,
wherein said method has an apparatus comprising:
   a reinforced concrete, said reinforced concrete having a steel bar;
   a radioactive detecting device, said radioactive detecting device having a radiation source;
   an imaging device, said imaging device displaying an image of said reinforced concrete having said steel bar; and
   a data analyzer, said data analyzer analyzing said image.

8. The method according to claim 7,
wherein said reinforced concrete further selected from a group consisting of a reinforced concrete having a hole and a reinforced concrete having an artificial aperture.

9. The method according to claim 7,
wherein said steel bar has a length between 12 cm and 18 cm, a diameter between 1 cm and 1.5 cm and a thickness of a protecting layer between 3 cm and 8 cm.

10. The method according to claim 7,
wherein said radiation source radiates a ray selected from a group consisting of Ir-192, Co-60 and Cs-137; and
wherein said ray has a radiation intensity between 68 Ci and 82 Ci.

* * * * *